US007253254B1

(12) United States Patent
Sebald

(10) Patent No.: US 7,253,254 B1
(45) Date of Patent: Aug. 7, 2007

(54) POLYPEPTIDE VARIANTS WITH INCREASED HEPARIN-BINDING CAPACITY

(75) Inventor: Walter Sebald, Wuerzburg (DE)

(73) Assignee: Osteopharma Inc., Osaka (JP)

( * ) Notice: Subject to any disclaimer, the term of this patent is extended or adjusted under 35 U.S.C. 154(b) by 0 days.

(21) Appl. No.: 09/913,467

(22) PCT Filed: Jan. 27, 2000

(86) PCT No.: PCT/EP00/00637

§ 371 (c)(1),
(2), (4) Date: Dec. 11, 2001

(87) PCT Pub. No.: WO00/47736

PCT Pub. Date: Aug. 17, 2000

(30) Foreign Application Priority Data

Feb. 13, 1999 (DE) ................................ 199 06 096

(51) Int. Cl.

| | |
|---|---|
| ***A61K 38/00*** | (2006.01) |
| ***C07K 1/00*** | (2006.01) |
| ***C07K 14/00*** | (2006.01) |
| ***C07H 19/00*** | (2006.01) |
| ***C07H 21/04*** | (2006.01) |

(52) U.S. Cl. ...................... 530/300; 530/350; 530/351; 536/22.1; 536/23.1; 536/23.51

(58) Field of Classification Search ................ 530/322, 530/324, 350; 435/69.1, 320.1, 325
See application file for complete search history.

(56) References Cited

U.S. PATENT DOCUMENTS 4,455,256 A 6/1984 Urist
4,804,744 A 2/1989 Sen
4,877,864 A 10/1989 Wang et al.
4,968,590 A 11/1990 Kuberasampath et al.
5,011,691 A 4/1991 Oppermann et al.
5,013,649 A 5/1991 Wang et al.
5,106,748 A 4/1992 Wozney et al.
5,116,738 A 5/1992 Wang et al.
5,141,905 A 8/1992 Rosen et al.
5,166,058 A 11/1992 Wang et al.
5,168,050 A 12/1992 Hammonds, Jr. et al.
5,187,076 A 2/1993 Wozney et al.
5,194,596 A * 3/1993 Tischer et al. .............. 530/399
5,250,302 A 10/1993 Oppermann et al.
5,258,494 A 11/1993 Oppermann et al.
5,266,683 A 11/1993 Oppermann et al.
5,318,898 A 6/1994 Israel
5,324,819 A 6/1994 Oppermann et al.
5,344,654 A 9/1994 Rueger et al.
5,350,836 A * 9/1994 Kopchick et al. ........... 530/399
5,354,557 A 10/1994 Oppermann et al.
5,364,839 A 11/1994 Gerhart et al.
5,366,875 A 11/1994 Wozney et al.
5,385,887 A 1/1995 Yim et al.
5,393,739 A 2/1995 Bentz et al.
5,399,677 A 3/1995 Wofman et al.
5,459,047 A 10/1995 Wozney et al.
5,496,552 A 3/1996 Kuberasampath et al.
5,510,418 A 4/1996 Rhee et al.
5,516,654 A 5/1996 Israel
5,597,897 A 1/1997 Ron et al.
5,618,924 A 4/1997 Wang et al.
5,631,142 A 5/1997 Wang et al.
5,650,494 A 7/1997 Cerletti et al.
5,652,118 A 7/1997 Ozkaynak et al.
5,652,332 A * 7/1997 Little, II ..................... 530/324
5,670,338 A 9/1997 Murakami et al.
5,703,043 A 12/1997 Celeste et al.
5,707,962 A 1/1998 Chen et al.
5,739,277 A 4/1998 Presta et al.
5,750,651 A 5/1998 Oppermann et al.
5,770,444 A 6/1998 Lee et al.
5,801,014 A 9/1998 Lee et al.
5,804,416 A 9/1998 Wolfman et al.
5,814,604 A 9/1998 Oppermann et al.
5,827,733 A 10/1998 Lee et al.
5,834,179 A 11/1998 Jones et al.

(Continued)

FOREIGN PATENT DOCUMENTS

DE 19548476 A1 6/1997
EP 242 466 B1 4/1986
EP 0 414 915 A 3/1991
EP 148 155 B1 12/1991
EP 409 472 B1 11/1994

(Continued)

OTHER PUBLICATIONS

Linkhart, T., et al. Growth factors for bone growth and repair: IGF, TGF-beta, and BMP. Bone, 1996, vol. 19, suppl. 1, pp. 1S-12S.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, p. 491-495.*
Ruppert et al., Eur J. Biochem Apr. 1, 1996; 237(1):295-302.*

(Continued)

*Primary Examiner*—Marianne P. Allen
*Assistant Examiner*—Cherie Woodward
(74) *Attorney, Agent, or Firm*—Townsend and Townsend and Crew, LLP

(57) ABSTRACT

The invention pertains to polypeptide variants with increased heparin-binding ability. Increased heparin-binding ability is achieved by addition, insertion, and/or substitution of an amino acid sequence $X_1X_2X_3X_4X_5X_6$ (SEQ ID NO. 1 or NO.2). Polypeptide variants according to the invention are particularly suited for stimulation of chondrogenesis, osteogenesis, and wound healing. The invention also pertains to amino acid molecules that encode said polypeptide variants, host cells containing said nucleic acid molecules, and processes for producing the polypeptide variants.

28 Claims, 10 Drawing Sheets

U.S. PATENT DOCUMENTS

| | | | | |
|---|---|---|---|---|
| 5,840,325 | A | 11/1998 | Kuberasampath et al. | |
| 5,849,880 | A | 12/1998 | Wozney et al. | |
| 5,863,758 | A | 1/1999 | Oppermann et al. | |
| 5,866,364 | A | 2/1999 | Israel et al. | |
| 5,902,785 | A | 5/1999 | Hattersley et al. | |
| 5,958,441 | A | 9/1999 | Oppermann et al. | |
| 5,984,967 | A | 11/1999 | Zdeblick et al. | |
| 5,994,094 | A | 11/1999 | Hotten et al. | |
| 6,057,430 | A | 5/2000 | Cerletti | |
| 6,071,708 | A | 6/2000 | Jones et al. | |
| 6,080,779 | A | 6/2000 | Gasper et al. | |
| 6,120,760 | A | 9/2000 | Hotten et al. | |
| 6,150,328 | A | 11/2000 | Wang et al. | |
| 6,180,602 | B1 | 1/2001 | Kato et al. | |
| 6,180,605 | B1 | 1/2001 | Chow et al. | |
| 6,180,606 | B1 | 1/2001 | Chow et al. | |
| 6,190,880 | B1 | 2/2001 | Isreal et al. | |
| 6,197,550 | B1 | 3/2001 | Hotten et al. | |
| 6,207,813 | B1 | 3/2001 | Wozney et al. | |
| 6,245,889 | B1 | 6/2001 | Wang et al. | |
| 6,261,835 | B1 | 7/2001 | Oppermann et al. | |
| 6,297,213 | B1 | 10/2001 | Oppermann et al. | |
| 2001/0020086 | A1* | 9/2001 | Hubbell et al. | 530/322 |

FOREIGN PATENT DOCUMENTS

| | | | |
|---|---|---|---|
| EP | 473 649 | B1 | 2/1995 |
| EP | 411 105 | B1 | 6/1995 |
| EP | 427 732 | B1 | 7/1995 |
| EP | 451 147 | B1 | 8/1995 |
| EP | 608 211 | B1 | 12/1995 |
| EP | 362 367 | B1 | 2/1996 |
| EP | 535 091 | B1 | 4/1996 |
| EP | 313 578 | B1 | 8/1996 |
| EP | 372 031 | B1 | 9/1996 |
| EP | 591 392 | B1 | 9/1996 |
| EP | 384 731 | B1 | 12/1996 |
| EP | 394 418 | B1 | 4/1997 |
| EP | 429 570 | B1 | 1/1998 |
| EP | 448 704 | B1 | 6/1998 |
| EP | 643 767 | B1 | 7/1998 |
| EP | 687 270 | B1 | 5/2000 |
| EP | 625 989 | B1 | 1/2001 |
| EP | 733 108 | B1 | 4/2001 |
| EP | 575 555 | B1 | 7/2001 |
| EP | 536 186 | B1 | 11/2001 |
| EP | 688 360 | B1 | 11/2001 |
| WO | WO91/18558 | A | 12/1991 |
| WO | WO96/39430 | | 12/1996 |
| WO | WO97/06254 | | 2/1997 |
| WO | WO 97/27296 | A1 | 7/1997 |
| WO | WO97/47312 | A | 12/1997 |
| WO | WO 98/15179 | A1 | 4/1998 |
| WO | WO 01/76532 | A2 | 10/2001 |

OTHER PUBLICATIONS

Skolnick et al. 2000, Trends in Biotech. 18:34-39.*
Bork, 2000, Genome Research 10:398-400.*
Doerks et al. 1998, Trends in Genetics 14:248-250.*
Smith et al. 1997, Nature Biotechnology 15:1222-1223.*
Brenner. 1999, Trends in Genetics 15:132-133.*
Bork et al. 1996, Trends in Genetics 12:425-427.*
Benjamin et al., 1998, Development 125:1591-1598; see Abstract and pp. 1594-1596.*
Vukicevic et al. 1996, PNAS USA 93:9021-9026.*
Massague. 1987, Cell 49:437-8.*
Pilbeam et al., 1993, Bone 14:717-720.*
Meddahi et al., Path Res Pract. 1994. 190:923-928.*
Jay Gropp, et al.: "Biochemical and Biophiysical Characterization of Refolded *Drosophila* DPP, a Homolog of Bone Morphogenetic Proteins 2 and 4" *Journal of Biochemistry,* vol. 273 (44) Oct. 30, 1998, pp. 29052-29065.
N. R. Küber, et al.: "Inductive properties of recombinant human BMP-2 produced in bacterial expression system," *Intl. Journal of Oral Maxillofacial Surgery,* (Aug. 1998), vol. 27 (4) pp. 305-309.
R. Ruppert, et al.: "Human bone morphgenetic protein 2 contains a heparin-binding site which modifies its biological activity" *Eur. J. Biochem.* vol. 237 (1996) pp. 295-302.
J.R. From, et al.: "Differences in the interaction of heparin with arginine and lysine and the importance of the basic amino acids in the binding hepain to acidic fibroblast growth factor" *Archives of Biochemistry and Biophysics,* vol. 323(2), Nov. 10, 1995, pp. 279-287.
E. Albert, et al.: "Pigment epithelium-derived factor (PEDF) binds to glycosaminoglycans: analysis of th binding site" vol. 37 (1998) pp. 10643-40652.
Arnason et al., "*Homo sapiens* mitochondrial DNA, complete genome," abstract, X93334, X93334.1, XP-002230776, pp. 1-8 (1996).

* cited by examiner dermatan sulfate keratan sulfate chondroitin-6-sulfate heparan sulfate hyaluronic acid

| | BMP-2 | T3 | T4 |
|---|---|---|---|
| EC50 (nM) | 13 | 29 | 69 |

| | BMP-2 | T3 | T4 |
|---|---|---|---|
| EC50 (nM) | 38 | 91 | 95 |

a b

SEQUENCE LISTING

<160> NUMBER OF SEQ ID NOS: 12

<210> SEQ ID NO 1
<211> LENGTH: 6
<212> TYPE: PRT
<213> ORGANISM: Artificial sequence
<220> FEATURE:
<221> NAME/KEY: MUTAGEN
<222> LOCATION: (1)
<223> OTHER INFORMATION: K, R or H
<220> FEATURE:
<221> NAME/KEY: MUTAGEN
<222> LOCATION: (2)
<223> OTHER INFORMATION: K, R or H
<220> FEATURE:
<221> NAME/KEY: MUTAGEN
<222> LOCATION: (3)
<223> OTHER INFORMATION: K, R, H or no amino acid
<220> FEATURE:
<221> NAME/KEY: MUTAGEN
<222> LOCATION: (4)
<223> OTHER INFORMATION: not K, R, H, but any other amino acid
<220> FEATURE:
<221> NAME/KEY: MUTAGEN
<222> LOCATION: (5)
<223> OTHER INFORMATION: not K, R, H, but any other or no amino acid
<220> FEATURE:
<221> NAME/KEY: MUTAGEN
<222> LOCATION: (6)
<223> OTHER INFORMATION: not K, R, H, but any other or no amino acid
<220> FEATURE:
<223> OTHER INFORMATION: description artificial sequence: Oligopeptide insert in polypeptide variant with increased heparin-binding ablity

<400> SEQUENCE: 1

Xaa Xaa Xaa Xaa Xaa Xaa
1 5

<210> SEQ ID NO 2
<211> LENGTH: 6
<212> TYPE: PRT

-continued

```
<213> ORGANISM: Artificial sequence
<220> FEATURE:
<223> OTHER INFORMATION: description artificial sequence: Oligopeptide
      insert in polypeptide variant with increased heparin-binding
      ablity
<220> FEATURE:
<221> NAME/KEY: MUTAGEN
<222> LOCATION: (1)
<223> OTHER INFORMATION: K, R or H
<220> FEATURE:
<221> NAME/KEY: MUTAGEN
<222> LOCATION: (2)
<223> OTHER INFORMATION: not K, R, H, but any other amino acid
<220> FEATURE:
<221> NAME/KEY: MUTAGEN
<222> LOCATION: (3)
<223> OTHER INFORMATION: K, R or H
<220> FEATURE:
<221> NAME/KEY: MUTAGEN
<222> LOCATION: (4)
<223> OTHER INFORMATION: not K, R, H, but any other amino acid
<220> FEATURE:
<221> NAME/KEY: MUTAGEN
<222> LOCATION: (5)
<223> OTHER INFORMATION: not K, R, H, but any other or no amino acid
<220> FEATURE:
<221> NAME/KEY: MUTAGEN
<222> LOCATION: (6)
<223> OTHER INFORMATION: not K, R, H, but any other or no amino acid

<400> SEQUENCE: 2

Xaa Xaa Xaa Xaa Xaa Xaa
  1               5


<210> SEQ ID NO 3
<211> LENGTH: 4
<212> TYPE: PRT
<213> ORGANISM: Artificial sequence
<220> FEATURE:
<223> OTHER INFORMATION: description artificial sequence:
      heparin-binding sequence

<400> SEQUENCE: 3

Arg Lys Arg Ala
  1


<210> SEQ ID NO 4
<211> LENGTH: 8
<212> TYPE: PRT
<213> ORGANISM: Artificial sequence
<220> FEATURE:
<223> OTHER INFORMATION: description artificial sequence:
      heparin-binding sequence

<400> SEQUENCE: 4

Arg Lys Arg Ala Lys His Lys Gln
  1               5


<210> SEQ ID NO 5
<211> LENGTH: 120
<212> TYPE: PRT
<213> ORGANISM: Artificial sequence
<220> FEATURE:
<223> OTHER INFORMATION: description artificial sequence: T3

<400> SEQUENCE: 5

Met Ala Gln Ala Lys His Lys Gln Arg Lys Arg Ala Arg Lys Arg Leu
  1               5                  10                  15

Lys Ser Ser Cys Lys Arg His Pro Leu Tyr Val Asp Phe Ser Asp Val
             20                  25                  30
```

-continued

```
Gly Trp Asn Asp Trp Ile Val Ala Pro Pro Gly Tyr His Ala Phe Tyr
        35                  40                  45

Cys His Gly Glu Cys Pro Phe Pro Leu Ala Asp His Leu Asn Ser Thr
    50                  55                  60

Asn His Ala Ile Val Gln Thr Leu Val Asn Ser Val Asn Ser Lys Ile
65                  70                  75                  80

Pro Lys Ala Cys Cys Val Pro Thr Glu Leu Ser Ala Ile Ser Met Leu
                85                  90                  95

Tyr Leu Asp Glu Asn Glu Lys Val Val Leu Lys Asn Tyr Gln Asp Met
            100                 105                 110

Val Val Glu Gly Cys Gly Cys Arg
        115                 120


<210> SEQ ID NO 6
<211> LENGTH: 124
<212> TYPE: PRT
<213> ORGANISM: Artificial sequence
<220> FEATURE:
<223> OTHER INFORMATION: description artificial sequence:T4

<400> SEQUENCE: 6

Met Ala Gln Ala Lys His Lys Gln Arg Lys Arg Ala Lys His Lys Gln
 1               5                  10                  15

Arg Lys Arg Leu Lys Ser Ser Cys Lys Arg His Pro Leu Tyr Val Asp
            20                  25                  30

Phe Ser Asp Val Gly Trp Asn Asp Trp Ile Val Ala Pro Pro Gly Tyr
        35                  40                  45

His Ala Phe Tyr Cys His Gly Glu Cys Pro Phe Pro Leu Ala Asp His
    50                  55                  60

Leu Asn Ser Thr Asn His Ala Ile Val Gln Thr Leu Val Asn Ser Val
65                  70                  75                  80

Asn Ser Lys Ile Pro Lys Ala Cys Cys Val Pro Thr Glu Leu Ser Ala
                85                  90                  95

Ile Ser Met Leu Tyr Leu Asp Glu Asn Glu Lys Val Val Leu Lys Asn
            100                 105                 110

Tyr Gln Asp Met Val Val Glu Gly Cys Gly Cys Arg
        115                 120


<210> SEQ ID NO 7
<211> LENGTH: 374
<212> TYPE: DNA
<213> ORGANISM: Artificial sequence
<220> FEATURE:
<223> OTHER INFORMATION: description artificial sequence:T3
      (nucleic acid sequence)

<400> SEQUENCE: 7

ccatggctca agccaaacac aaacagcgga aacgcgctcg taaacgtctt aagtccagct      60

gtaagagaca ccctttgtac gtggacttca gtgacgtggg gtggaatgac tggattgtgg     120

ctcccccggg gtatcacgcc ttttactgcc acggagaatg cccttttcct ctggctgatc     180

atctgaactc cactaatcat gccattgttc agacgttggt caactctgtt aactctaaga     240

ttcctaaggc atgctgtgtc ccgacagaac tcagtgctat ctcgatgctg taccttgacg     300

agaatgaaaa ggttgtatta aagaactatc aggacatggt tgtggagggt tgtgggtgtc     360

gctagtaagg atcc                                                       374


<210> SEQ ID NO 8
```

-continued

<211> LENGTH: 386
<212> TYPE: DNA
<213> ORGANISM: Artificial sequence
<220> FEATURE:
<223> OTHER INFORMATION: description artificial sequence: T4
(nucleic acid sequence)

<400> SEQUENCE: 8
ccatggctca agccaaacac aaacagcgga aacgcgctaa gcataagcaa cgtaagcgtc 60
ttaagtccag ctgtaagaga caccctttgt acgtggactt cagtgacgtg ggtggaatg 120 actggattgt ggctcccccg gggtatcacg ccttttactg ccacggagaa tgccctttc 180 ctctggctga tcatctgaac tccactaatc atgccattgt tcagacgttg gtcaactctg 240
ttaactctaa gattcctaag gcatgctgtg tcccgacaga actcagtgct atctcgatgc 300
tgtaccttga cgagaatgaa aaggttgtat taaagaacta tcaggacatg gttgtggagg 360
gttgtgggtg tcgctagtaa ggatcc 386

<210> SEQ ID NO 9
<211> LENGTH: 47
<212> TYPE: DNA
<213> ORGANISM: Artificial sequence
<220> FEATURE:
<223> OTHER INFORMATION: description artificial sequence: Insert
between NcoI and AflII restriction sites

<400> SEQUENCE: 9
catggctcaa gccaaacaca aacagcggaa acgcgctcgt aaacgtc 47

<210> SEQ ID NO 10
<211> LENGTH: 47
<212> TYPE: DNA
<213> ORGANISM: Artificial sequence
<220> FEATURE:
<223> OTHER INFORMATION: description artificial sequence: Insert
between NcoI and AflII restriction sites

<400> SEQUENCE: 10
ttaagacgtt tacgagcgcg tttccgctgt ttgtgtttgg cttgagc 47

<210> SEQ ID NO 11
<211> LENGTH: 59
<212> TYPE: DNA
<213> ORGANISM: Artificial sequence
<220> FEATURE:
<223> OTHER INFORMATION: description artificial sequence: Insert
into BMP-2 cDNA

<400> SEQUENCE: 11
catggctcaa gccaaacaca aacagcggaa acgcgctaag cataagcaac gtaagcgtc 59

<210> SEQ ID NO 12
<211> LENGTH: 59
<212> TYPE: DNA
<213> ORGANISM: Artificial sequence
<220> FEATURE:
<223> OTHER INFORMATION: description artificial sequence: Insert
into BMP-2 cDNA

<400> SEQUENCE: 12
ttaagacgct tacgttgctt atgcttagcg cgtttccgct gtttgtgttt ggcttgagc 59

POLYPEPTIDE VARIANTS WITH INCREASED HEPARIN-BINDING CAPACITY

The present invention pertains to polypeptide variants with increased heparin-binding ability. Furthermore, the present invention pertains to nucleic acid molecules encoding these variants, the host cells containing the nucleic acid molecules, and the processes used to produce polypeptide variants and recombinant polypeptide variants. Also, the present invention pertains to the use of polypeptide variants to stimulate chondrogenesis, osteogenesis, and wound healing, and to treat inflammation and cancer. In addition, the present invention pertains to osteoinductive compositions containing these variants.

Numerous biological factors influence the development and regeneration of cells, tissues, and organs of the human and animal body. Even today, many of these factors are still unknown, and the processes they control are not yet completely understood. Bone formation (osteogenesis) is a process that is as yet not completely understood; it can be broken down into numerous consecutive single processes, such as, for example, chemotaxis, mitosis, and differentiation. Chemotaxis, in this context, means the direct migration of cells in response to a chemical gradient of signal connections that are released from the insoluble demineralized bone matrix, consisting primarily of type I insoluble collagen. Type I insoluble collagen binds plasma fibronectin which itself contains domains that bind collagen, fibrin, and heparin.

There are principally two main groups of biologically active factors that control osteogenesis, those that are systemically active and those that are locally active.

The group of systemically active factors includes; for example, the two hormones PTH (parathyroid hormone) and 1,25-dihydroxy-vitamin D, which regulate endogenic calcium levels. An additional hormone involved in osteogenesis is calcitonin, which prevents bone resorption.

Estrogens, androgens, growth hormones, insulin-like growth factor (IGF), thyroid hormones, and glucocorticoids, for example, are also among the systemic hormones that regulate osteogenesis.

The group of locally active factors encompasses (i) cytokines that effect bone decomposition such as IL-1, tumor necrosis factor (TNF), IL-6, IL-11, and ODF (osteoclastic differentiation factor, TRANCE);

(ii) cytokines that prevent bone decomposition: IL4, IL-13, IL-18, IFN (interferon), OPG (osteoprotegerin), and IL-1 ra (interleukin-1-receptor antagonist);

(iii) colony-stimulating factors: M-CSF (macrophage-colony stimulating factor) and GM-CSF (granulocyte-macrophage stimulating factor);

(iv) prostaglandins, leukotrienes, and nitrogen monoxide; and (v) growth factors: IGF (insulin-like growth factor), proteins from the decapentaplegic-Vg-related (DVR) family including the proteins of the TGF-β (transforming growth factor β) superfamily, which encompasses the proteins of the activin/inhibin family, MIS (Mullerian inhibitory substance), GDF (growth/differentiation factor), nodal, and dorsalin; FGF (fibroblast growth factor), PDGF (platelet-derived growth factor), and PTHrP (PTH-related protein; parathyroid hormone-related protein).

In the context of the present invention, the TGF-β superfamily is of particular interest.

At this point in time, the TGF-β superfamily comprises more than twenty proteins, not counting the suspected orthologs in various organisms. Along with the TGF-βs, the BMPs (bone morphogenetic proteins), the GDFs (growth differentiation factors) inhibins/activins, and other proteins (Kingsley, 1994) belong to the superfamily. They all consist of two sub-units that are almost always homodimers of two identical monomers, covalently linked by a disulfide bridge.

One characterizing feature of all proteins of the TGF-β superfamily structurally studied up to the present is the "TGF-β/BMP structure", which consists of a cysteine knot, an α-helix, and at least four β-strands per monomer, resulting in a typical arrangement of the monomers in the dimer (McDonald and Hendrickson, 1993). The amino acid sequences can vary considerably and sometimes resemble each other with fewer than 40% identical positions. The "loop" areas as well as the N-terminal sequences are particularly variable. Nonetheless, a surprising degree of conservation of function and structure has been shown for the evolution of all the members of the TGF-β superfamily. They all contain a structural element designated as the "cysteine knot" that consists of three disulfide bridges which are conserved and identically arranged in all the proteins of the TGF-β superfamily. Apart from the TGF-βs, representative members that have been particularly well studied are the individual members of the BMPs such as BMP-2 and BMP-7, and members of the GDFs such as GDF-5, which can turn on the development and regeneration of bones and cartilage tissue. Thus for example, BMP-2 has been shown to display osteoinductive properties in heterotopic as well as orthotopic implants.

The proteins of the TGF-β superfamily are synthesized within the cell initially as one large proprotein from which the mature protein is created by proteolysis. It seems that after an ArgXXArg recognition sequence the proprotein is cleaved off so that a C-terminal sequence of about 100 to 140 amino acid residues, which represent the mature protein, is released.

For signal transduction the factors belonging to the TGF-β superfamily bind to the extra-cellular domains of two types of membrane receptors of their target cells, e.g. inducible bone marrow stem cells. The type 2 sub-unit contains within its cytoplasmatic part a protein serine kinase, which upon ligand binding within the type 1 sub-unit phosphorylates serine residues. This also activates within the type 1 sub-unit a protein serine kinase, which can phosphorylate and activate intracellular signal proteins such as SMADs. There are indications that sub-units of both type 1 and type 2 exist as dimers. Recently, the crystal structure of the extracellular domain of the type 2 sub-unit of the activin receptor (Act-RII) was determined. BMP-2, which is among the best studied proteins of the TGF-β family, binds to the receptor sub-units via the structurally highly conserved domain after the first cysteine of the cysteine knot. The highly variable N-terminal sequence before the first cysteine of the cysteine knot does not directly interact in BMP-2 with the receptor sub-units. The interaction of proteins of the TGF-β superfamily with type 1 and type 2 receptor sub-units is partly promiscuous and the specifities are overlapping. It is not yet clear to what extent there is common usage of receptor sub-units or to what extent there are differences in the mechanism of receptor activation. In particular, current literature does not unequivocally reveal which structural elements determine the specificity of a protein, e.g. for osteoinductive activity.

The members of the TGF-β superfamily can interact with a number of other proteins other than the receptor sub-units. Thus, the activity of the members can be modulated or inhibited. Fetuin/α2-HS glycoprotein and a peptide derived from it (TRH1) bind BMP-2 and TGF-β, with BMP-2 being bound with higher affinity. This binding competes with the binding at the receptor. Mammalian noggin protein binds BMP-2 with a high affinity in competition with the receptor. As shown in *Xenopus laevis* oocytes, chordin acts as an inhibitor for BMP4. Follistatin binds with high affinity to activin and BMP-7. BMP-2 has been proven to be capable of binding to heparin.

The therapeutic potential of the members of the TGF-β superfamily is apparent due to their physiological significance. Recombinantly produced proteins are of particular interest, because they can be obtained in large quantities. Moreover, the nucleic acids that encode them are potential agents in gene therapy.

Thus, there is a general interest in members of the TGF-β superfamily and their variants with altered biological properties. Kübler et al. (1999) describe a BMP analog EHBMP-2 the primary structure of which differs from that of naturally occurring human BMP-2 in that the first twelve amino acids, which are considered responsible for the strong heparin binding of BMP-2, are replaced by the first thirteen amino acids of human interleukin-2. This genetically altered BMP-2 analog was recombinantly expressed in *E. coli.* EHBMP-2 reveals a negligible affinity to heparin and a higher biological activity in various cell cultures, i.e. in vitro. In comparing the in vivo activity of the variant with that of natural BMP-2, it was shown that in mouse at BMP-2 concentrations starting from 4 μg a heterotopic bone induction was produced in nearly all samples, whereas it took an amount of 40 μg of EHBMP-2 to achieve the same effect. Furthermore, it was found that the resulting extent of new bone formation at the same protein concentrations was significantly greater in natural BMP-2 than its BMP analog, EHBMP-2.

The object underlying the present invention is to provide further polypeptide variants that in vivo are equally or more effective than the wild type. A further object is to provide nucleic acids encoding the polypeptide variants, and vectors and host cells containing such nucleic acids. Furthermore, the present invention seeks to provide processes for producing the polypeptide variants. Finally, pharmaceutical compositions should be provided that contain these polypeptide variants, and also the use thereof.

According to the invention, this object is achieved by a polypeptide variant with increased heparin-binding ability, which is characterized in that (i) added to the amino acid sequence of a polypeptide with a low heparin-binding ability is at least one oligopeptide comprising the amino acid sequence $X_1X_2X_3X_4X_5X_6$, and/or (ii) inserted into the amino acid sequence of a polypeptide is at least one oligopeptide comprising the amino acid sequence $X_1X_2X_3X_4X_5X_6$, and/or (iii) at least one oligopeptide sequence naturally occurring within the amino acid sequence of a polypeptide is substituted by an oligopeptide comprising the amino acid sequence $X_1X_2X_3X_4X_5X_6$, wherein:

$X_1$=K, R, or H;

$X_2$=K, R, or H;

$X_3$=K, R, H, or no amino acid;

$X_4$=not K, R, H, but any other amino acid;

$X_5$=not K, R, H, but any other or no amino acid;

$X_6$=not K, R, H, but any other or no amino acid (SEQ ID No: 1), or:

$X_1$=K, R, or H;

$X_2$=not K, R, H, but any other amino acid;

$X_3$=K, R, or H;

$X_4$=not K, R, H, but any other amino acid;

$X_5$=not K, R, H, but any other or no amino acid;

$X_6$=not K, R, H, but any other or no amino acid (SEQ ID No: 2).

Below, a few terms will be explained in more detail to clarify how they are to be understood in the context of the present application.

The term "polypeptide" as it is used below in the description, comprises peptides or proteins consisting of 5 or more amino acids and having at least one biological activity. Furthermore, the term comprises biologically active fragments of polypeptides, and their mutants and fusion proteins.

"Polypeptide variant with increased heparin-binding ability" means that the polypeptide variant shows increased ability to bind heparin greater than that of the unaltered polypeptide. Generally, the ability to bind heparin can be measured by, for example, plasma resonance analysis with the aid of a heparin coated carrier. The individual experimental conditions are described for example in Ruppert et al., 1996.

In vivo efficiency is understood to mean the extent of the intended effect at the target site. The in vivo efficiency is determined by the biological activity of the protein in conjunction with the availability of the protein at the target site. In the final analysis, it is measured as the effect at the target site. Established methods may be used to measure the effect. In the case of BMP-2 variants, the induction of ectopic bone formation, as described in Kübler & Urist, 1991, and Kübler et al., 1999, has turned out to be useful.

A biologically active polypeptide that modulates growth and/or the differentiation of cells is called a "growth factor".

To the extent reference is made in the following to specific polypeptides, their amino acid sequences are obtainable, for example, from the publicly available database Entrez (currently http://www.ncbi.nlm.nih.gov/Entrez/).

The expression "homology" known to the person skilled in the art denotes the degree of relatedness between two or more polypeptides defined by conformity between amino acid sequences using known processes such as computer-assisted sequence comparisons (basic local alignment search tool, S. F. Altschul et al., J. Mol. Biol. 215 (1990), 403-410). The percentage of "homology" is determined by the percentage of identical regions in two or more sequences while also considering gaps or other sequence peculiarities. As a rule, special computer programs are used with algorithms that meet the specific demands.

Preferred processes to determine homology first generate the greatest conformity between the sequences under investigation. Computer programs to determine homology between two sequences include, but are not limited to the GCG program package, including GAP (Devereux, J. et al., Nucleic Acids Research 12 (12): 387 (1984); Genetics Computer Group University of Wisconsin, Madison, (WI)); BLASTP, BLASTIN, and FASTA (Altschul, S. et al., J. Mol. Biol. 215:403-410) (1990)). The program BLASTX can be obtained from the National Centre for Biotechnology Information (NCBI) and from other sources (BLAST Manual, Altschul, S. et al., NCB NLM NIH Bethesda, Md. 20894; Altschul, S. et al., Mol. Bio. 215:403-410 (1990)). The well-known Smith-Waterman algorithm can be used to determine homologies.

Preferred parameters for the comparison of amino acid sequences are as follows:

| | |
|---|---|
| Algorithm: | Needleman and Wunsch, J. Mol. Biol. 48:443-453 (1970) |
| Comparison matrix: | BLOSUM 62 from Henikoff and Henikoff, PNAS USA 89 (1992), 10915-10919 |
| Gap Penalty: | 12 |
| Gap Length Penalty: | 4 |
| Threshold of Similarity: | 0 |

The GAP program is also suited for use with the above parameters. The above parameters are default parameters for amino acid sequence comparisons, in the case of which gaps at the ends do not reduce the homology value. With very short sequences relative to the reference sequence, it may also be necessary to increase the expectation value to 100,000 and in some cases reduce the word size to two.

Further exemplary algorithms, gap opening penalties, gap extension penalties, comparison matrices, including those named in the programming manual, Wisconsin package, Version 9, September 1997, can be used. The selection will depend on the comparison to be made, and further on whether the comparison is made between sequence pairs, in which case GAP or Best Fit would be preferred, or between a sequence and an extensive sequence database, in which case FASTA or BLAST would be preferred.

A conformity of 60% determined by using the above mentioned algorithm is designated in this application as 60% homology. Higher degrees of homology would be treated accordingly.

"His-tag" denotes a sequence of at least 6 histidine amino acids that through suitable cloning and fusion with an expressible sequence gives rise to a fusion protein with at least 6 histidine residues at the $NH_2$-terminus that can easily be purified by forming a complex with a $Ni^{2+}$ column.

"Heterologous gene" is to mean the coding region of a structure gene that either is not expressed under the control of its own homologous promoter or is not expressed within the organism from which it is derived, or is expressed neither under the control of its own promoter nor in the original organism.

"Cloning" comprises all cloning methods known from the prior art that can be applied here but that are not all described in detail, because they belong to the standard methods of the person skilled in the art.

"Recombinant expression in a suitable host cell" is to mean all expression methods known from the prior art in known expression systems that can be applied here, but are not all described in detail, because they belong to the standard methods of the person skilled in the art.

Surprisingly, it has been found that a polypeptide variant of this invention showed a higher heparin-binding ability than the unaltered polypeptide in that at least one oligopeptide containing an amino acid sequence according to the invention is added to and/or inserted into the polypeptide, and/or replaces some of the amino acids as polypeptides. It could be shown that in comparison to the unaltered polypeptide the amount of the variants bound to heparin was greater and that there was also less dissociation of the variants from heparin. Because heparin-like structures are integral components of the bone structure, the polypeptide variants of the invention also exhibit an increased binding capacity for bone structures. This property is especially important for regenerative processes in the bone structure, where in this case the polypeptides concerned participate in bone morphogenesis (osteogenesis). It could be shown that the polypeptide variants of the invention increased heparin-binding ability by a factor of 30, but at least by a factor of 10. The increased heparin-binding ability in turn led to a dramatically increased in vivo efficiency, as demonstrated for example in FIG. 8.

As mentioned above, the effect of the polypeptides participating in osteogenesis is imparted by receptors that are located, inter alia, on the surface of inducible bone marrow stromal stem cells. The latter have the ability to form bone cells upon the influence of an inductive signal from morphogenetic proteins or demineralized bone matrix. Without wanting to be bound to this theory, it is assumed that the increase in heparin-binding ability of polypeptides, particularly of osteoinductive polypeptides results in an increase of the local concentration of osteogenetic proteins in the immediate vicinity of the location of osteogenesis.

However, because heparin competes with the cellular receptor of the polypeptide for the polypeptide variant, it must first be assumed that the increased heparin-binding ability of the polypeptide variant will decrease the amount of polypeptide available to the polypeptide-specific receptor and thus lead to a decrease in signal transduction.

Surprisingly, it has been found that the biological availability of the polypeptide variant is not affected by the simultaneous increase in heparin-binding ability, but rather that the increased heparin-binding ability correlates with an increase in the local concentration of polypeptide available for the specific receptor.

Furthermore, it has surprisingly been found that the bone formed by the polypeptide variant in vivo is of better quality than that formed by the unaltered polypeptide.

In a preferred embodiment, the amino acid sequence according to the invention is added to the N-terminus of the mature polypeptide, and/or inserted by substitution or insertion into the N-terminal region of the polypeptide. The N-terminal region means the first 20, preferably the first five, N-terminal amino acids.

To the extent that the polypeptide belongs to the TGF-β superfamily, the mature polypeptides, starting with BMP-2, for example, can be ascertained in the following manner: A search in the "Swiss-Prot" database (currently expasy.hcuge.ch/cgi-bin/sprot-search-de) with the search key word "BMP-2" reveals the amino acid sequence for the entire proprotein of human BMP-2 under the number P12643. From this, one can select the sequence for the mature protein under "bone morphogenetic protein 2". It correlates to amino acid residues 283-396. In order to identify the other proteins of the TGF-β superfamily, one submits this sequence 283-396 under "BLAST2" at EMBnet-CH (Lausanne, Switzerland). Databases Swiss-Prot+TrEMBL+TrEMBL_New are there searched for it with the program "blastp". Using the comparison matrix Blosum 62, one ascertains the 250 closest relatives to the protein. The program provides the corresponding identity numbers of the Swiss-Prot database under which one can find the amino acids of the entire proproteins. The sequence segments for the mature proteins are each indicated. They could also be derived, because the mature proteins are normally cleaved off after the recognition sequence RXXR (where X is any amino acid).

As mentioned earlier, all polypeptides of the TGF-β superfamily are characterized by a structural element designated as "cysteine knot" (McDonald and Hendrickson, 1993). For a protein belonging to this superfamily, the entire region in front of the cysteine knot represents the N-terminal region, and the amino acid sequence according to the invention is to be inserted preferably in front of the cysteine knot.

In an especially preferred embodiment, the oligopeptide containing the amino acid sequence according to the invention is inserted one to four times via addition, insertion, and/or substitution into the polypeptide, whereby one or more copies of the oligopeptide can be inserted at one or more positions into the polypeptide.

In an especially preferred embodiment, the oligopeptide has the sequence RKRA (SEQ ID No. 3) or the sequence RKRAKHKQ (SEQ ID No. 4).

Furthermore, it is preferred that the polypeptide variant contains at the N-terminus a sequence appropriate for the recombinant expression which would be M or MZ where M means methionine and Z means one or a plurality of any desired amino acids. For example, MZ could represent a signal sequence as known to one skilled in the art for many prokaryotic or eukaryotic proteins. It could be a signal sequence adapted to a given expression system, or a "homologous" signal sequence, i.e. one naturally belonging to the protein, and finally a combination of any signal sequence with purposefully inserted protease cleavage sites, etc.

Furthermore, it is preferred that the polypeptide variant contains a His-tag. The His-tag at the $NH_2$-terminus of the polypeptide variant significantly facilitates the purification of the protein, as said purification can be carried out at a nickel column via chelate formation.

The polypeptide underlying the polypeptide variant shows biological activity. Principally, all biological activities are important in the case of which the efficiency of a polypeptid with biological activity is limited by the diffusing of negatively charged intracellular and extracellular structures. Preferably, these negatively charged structures are structures of the extracellular matrix that are negatively charged due to their proteoglycan and glycoseaminoglycan content, like heparan, chondroitin sulfate, keratan sulfate, and dermatan sulfate. In a preferred embodiment, the biological activity regulates the development or differentiation of cells, tissues, and organs of the human or animal body.

What is here particularly preferred is that the polypeptide of the polypeptide variant regulates bone formation (osteogenetic activity). Osteogenetic activity can be measured, for example, by the growth factor-dependent incorporation of $^{35}SO_4$ into proteoglycan structures of limb buds of chicken embryos. A sensible concentration range is selected for the BMP protein to enable one to determine both the maximum cell response and $EC_{50}$ (concentration at which 50% of the maximum incorporation has been achieved). For assay conditions, see Ruppert et al., 1996.

Alternatively, the myoblastic mouse cell line C2C12 can be used to determine BMP-dependent induction of alkaline phosphatase (Katagiri et al., 1994). This test can also measure the maximal cell response and $EC_{50}$.

It is preferable to select the polypeptide from the group comprising hormones, cytokines, and growth factors. Particularly preferred are here: parathyroid hormone (PTH); calcitonin; growth hormone; insulin-like growth factor (IGF); cytokines that effect bone degeneration such as IL-1, tumor necrosis factor (TNF), IL-6, IL-11, and ODF (osteoclast differentiation factor, TRANCE); cytokines preventing bone degeneration: IL-4, IL-13, IL-18, IFN (interferon), OPG (osteoprotegerin) and IL-1ra (interleukin-1 receptor antagonist); colony stimulating factors: M-CSF (macrophage colony stimulating factor) and GM-CSF (granulocyte macrophage stimulating factor); and growth factors: IGF (insulin-like growth factor); proteins from the DVR family including those from the TGF-β (transforming growth factor β) superfamily, which comprises the activin/inhibin family, MIS (Mullerian inhibitory substance), GDF (growth/differentiation factor) family, nodal and dorsalin; FGF (fibroblast growth factor); PDGF (platelet-derived growth factor); and PTHrP (PTH-related protein).

Particularly preferred for the polypeptide are members of the TGF-β superfamily, activin/inhibin family, MIS, GDF family, nodal and dorsalin, and also members of the BMP family, particularly BMP-2, BMP-4, BMP-5, BMP-6, BMP-7/OP-1, or BMP-8/OP-2, as well as BMP-9, BMP-10, BMP-11, BMP-12, BMP-13, BMP-14, and BMP-15.

According to the invention, the above selection of growth factors is particularly important, because the roles of these factors in osteogenesis are known (Reddi, 1998); the use of inventive variants of these factors leads to increased heparin-binding ability while maintaining osteoinductive properties.

If the polypeptide belongs to the TGF-β superfamily and thus contains the above mentioned "cysteine knot structure", the inventive amino acid sequence is preferably inserted before the cysteine knot into the polypeptide sequence. Especially preferred positions include for example in BMP-2, the positions between the amino acid residues 2 and 3, 6 and 7, 10 and 11, and 13 and 14 of the mature protein. Due to the homology among the members of the TGF-β family, especially the conserved arrangement of the cysteines, the person skilled in the art will be able to determine positions corresponding to said proteins in other TGF-β family members.

The polypeptide may also be a hormone, a cytokine, or growth factor which shows an addition, substitution, insertion, inversion and/or deletions, whereby the polypeptide showing the addition, substitution, insertion, inversion and/or deletion shows at least 10%, preferably at least 50%, and particularly preferably at least 90% of the biological activity, in the case of osteogenetic polypeptides of the osteogenetic activity of the original polypeptide. Biological activity can in general be determined using any procedure known to the person skilled in the art to measure biological activity of the polypeptide.

In an additional preferred embodiment, the polypeptides obtained via addition, substitution, insertion, inversion, and/or deletion are at least 50%, preferably 75%, and particularly 90% homologous to the amino acid of the complete original polypeptide. In such cases, a biological activity of at least 10% may correlate with a minimum 50%, 75%, or 90% homology. The same may be true for a 50% or a 90% minimum biological activity.

Especially preferred are the polypeptide variants with amino acid sequences SEQ ID No. 5 (T3) and SEQ ID No 6 (T4). These polypeptide variants correspond to the polypeptide variants used in the examples showing increased efficiency at constant concentrations and improved quality of the induced bone, where improved quality means, in particular, increased density of the bone matrix and thus an increased biomechanical ability to bear weight.

In a further preferred embodiment, the polypeptide variant produced according to the invention is modified. The modifications consist of dimerizing, oligomerizing, and polymerizing the monomeric substrate, for example, by cross-linking with dicyclohexylcarbodiimide, pegylation, or association (self assembly). The resulting dimers, oligomers, and polymers can be separated, for example, by gel filtration. Further modifications comprise side chain modifications, for example, of ϵ-amino-lysine residues of the polypeptide variant, and amino-terminal or carboxy-terminal modifications. Finally, the term "modifications" comprises posttranslational events such as glycosylation or partial or complete deglycosylation of the protein.

Further, the invention provides nucleic acid molecules that comprise a nucleic acid sequence coding for a polypeptide variant according to the invention.

The nucleic acid sequence contained in the nucleic acid molecule according to the invention can be derived from genomic DNA, cDNA, or synthetic DNA, where synthetic DNA sequences would include those containing modified internucleoside bonds. Furthermore, nucleic acid sequences may also be RNA sequences, which may e.g. be required for expression via recombinant RNA vector systems.

Preferred nucleic acid molecules comprise a nucleic acid coding for one of the polypeptide variants T3 or T4. Examples of such nucleic acids are listed in the sequence listing under SEQ ID No. 7 (T3) and SEQ ID No. 8 (T4). Naturally, instead of those nucleic acid sequences listed under SEQ ID No. 7 or SEQ ID No. 8, one can use sequences that are based upon degeneration of the genetic code. In this context, the preferred nucleic acid sequences are those that in view of the expression in a particular host organism provide a codon selection suited to the codon use of this host organism. The invention also applies to the complementary sequences to those mentioned above.

In a preferred embodiment, the nucleic acid molecule according to the invention contains a promoter suitable for expression where the promoter controls the nucleic acid sequence. The selection of the promoter depends on the expression system used for expression. In general, inducible promoters such as for example the metallothionine promoter are preferred, but constitutive promoters are also possible.

In a further preferred embodiment, the nucleic acid molecule comprises at least part of a vector, particularly regulatory regions; the vector may be selected from bacteriophages such as λ-derivatives, adenoviruses, vaccinia viruses, baculo viruses, SV40 viruses, retroviruses, plasmids such as Ti plasmids of *Agrobacterium tumefaciens*, YAC vectors, and BAC vectors. Preferred vectors are $pR^{TS}pRC$ 109 (Weigel et al., 1989) and $pRBSIIPN_{25}x/o$ (Stueber, 1994).

Furthermore, the invention provides host cells that contain the nucleic acid molecule and that are suitable to express the nucleic acid molecule. In the prior art there are known a great number of prokaryotic and eukaryotic expression systems, the host cells being for example selected from prokaryotic cells, such as *E. coli* or *B. subtilis*, from eukaryotic cells, such as yeast cells, plant cells, insect cells, and mammalian cells, e.g. CHO cells, COS cells or HeLa cells, as well as their derivatives. From the prior art certain CHO producing strains are known, for example, whose patterns of glycosylation differ from those of the CHO cells. Polypeptide variants resulting from the use of glycosylation-efficient or glycosylation-diminished host cells may have an altered three-dimensional structure that itself may lead to an increased biological activity over that of the glycosylated polypeptide variant, provided that the polypeptide shows biological activity.

The subject matter of the present invention is also a process for producing a polypeptide variant with increased heparin-binding ability, the process comprising the following steps: adding at least one oligopeptide containing an amino acid sequence selected from SEQ ID No. 1 or SEQ No. 2, to the amino acid sequence of a polypeptide, and/or inserting at least one oligopeptide containing an amino acid sequence selected from SEQ ID No. 1 or SEQ No. 2, into the amino acid sequence of the polypeptide, and/or substituting at least one oligopeptide sequence naturally occurring within the amino acid sequence by an oligopeptide containing an amino acid sequence selected from SEQ ID No. 1 or SEQ ID No. 2.

The process can be performed by partial or total chemical synthesis, using the well-known Merrifield synthesis, or by enzymatic synthesis. Further, the process can be performed by way of gene technology, i.e. by recombinant expression. The invention also comprises the combination of chemical/enzymatic and gene technological processes.

In a preferred embodiment, the process comprises:

a) in vitro mutagenesis of a nucleic acid encoding a polypeptide such that
   (i) to the nucleic acid encoding the polypeptide is added at least one nucleic acid encoding an oligopeptide containing an amino acid sequence that is selected from SEQ ID No. 1 or SEQ ID No. 2; and/or
   (ii) into the nucleic acid encoding the polypeptide is inserted at least one nucleic acid encoding an oligopeptide containing the amino acid sequence that is selected from SEQ ID No. 1 or SEQ ID No. 2; and/or
   (iii) at least one nucleic acid sequence naturally occurring within the nucleic acid sequence encoding the polypeptide is substituted by a nucleic acid sequence encoding an oligopeptide containing an amino acid sequence selected from SEQ ID No. 1 or SEQ ID No. 2;
b) cloning of the mutated nucleic acid in a suitable expression vector;
c) transformation/transfection of a suitable host cell with the expression vector obtained;
d) cultivation of the transformed/transfected host cell under conditions suitable for expression;
e) isolation, and if necessary renaturation, of the expression products.

There are numerous procedures to express DNA sequences well known to the person skilled in the art; cf. Recombinant Gene Expression Protocols in Methods in Molecular Biology, Vol. 62, Humana Press Totowa, N.J. (1995). Expression can be both constitutive as well as inducible with inductors known to the person skilled in the art including, for example, IPTG and $Zn^{2+}$.

The nucleic acid sequences needed for mutagenesis, encoding a polypeptide with biological activity, can be found by screening cDNA libraries produced from tissue expressing the polypeptide, or by screening genomic DNA libraries with a detectably labeled specific probe. The identification of positive cDNA clones or genomic DNA clones follows standard procedures; cf. Maniatis et al., Molecular Cloning (1989), Cold Spring Harbor Laboratory Press. The nucleic acid sequence encoding the polypeptide containing the inventive amino acid sequence can be inserted into double-stranded DNA for example by cassette mutagenesis or by recombinant polymerase chain reaction (PCR). The corresponding methods are known to the person skilled in the art (e.g. Wang et al., 1997; Ruppert et al., 1996). The resulting mutated double-stranded DNA is then inserted into an expression vector.

Useful vectors and host cells have been described above. If expressed in *E. coli*, the protein can be removed from the insoluble part of the cells using guanidinium hydrochloride (Ruppert et al., 1996). Then, the polypeptide is renatured and purified via chromatography. For the purification of proteins of the TGF-β superfamily, a pH of eight is preferred, preferably at a high salt concentration (1 M NaCl), working in the presence of weak detergents with redox mediators.

Alternatively, the polypeptide variant can be harvested from culture medium if a suitable expression vector is used, resulting in the expression of a polypeptide variant with an appropriate secretory signal sequence.

The invention further provides pharmaceutical compositions that contain at least one polypeptide variant of the invention and physiologically compatible additives known from the prior art. Preferably, the polypeptide variant should be derived from a biologically active polypeptide, for example from a cytokine or growth factor. Hormones, cytokines, and growth factors involved in osteogenesis are especially preferred. The increased heparin-binding ability of the polypeptide variants leads to diminished diffusion of therapeutically active polypeptide variants away from the heparin component of demineralized bone matrix and thus to increased local concentrations of therapeutically active materials.

In general, an increased binding ability to extra-cellular matrix structures and cell surfaces has also been observed. Therapeutically active polypeptide variants can therefore be used to prevent and/or treat diseases involving or affecting the extracellular matrix or cell surfaces.

If the polypeptides underlying the polypeptide variants belong to the DVR family, they will be suitable to promote bone growth and bone repair. GDF-5 participation in cartilage formation has been described and it is postulated for the development of ligaments. Thus, GDF-5 derived polypeptide variants are suitable for repairing cartilage and ligaments. BMP-7/OP-1 suppresses the production of GDF-5, which possibly represents a mechanism to balance bone and cartilage formation. Thus, polypeptide variants derived from BMP-7 demonstrate regulatory properties in the context of bone and cartilage formation.

BMP-7 participates in kidney and eye development, BMP6 in skin development, and BMP-2 in heart development. Thus, according to this invention, polypeptide variants derived from BMP can be used to regulate kidney, eye, skin, and heart development.

Furthermore, GDF-5 induces angiogenesis. Therefore, GDF-5 derived polypeptide variants could be important in stimulating angiogenesis.

If the polypeptides of the polypeptide variants belong to the TGF-β family, the therapeutically efficient polypeptide variants are suitable for immune suppression, inflammation inhibition, and for stimulation of bone and cartilage formation. Due to increased depositing of extra-cellular matrix components such as collagens, fibronectins, glycosaminoglycans and proteoglycans, they are useful in wound healing. Furthermore, polypeptide variants based on TGF-β are useful to prevent detachment of the retina. Also, they can be advantageously applied to combat oral mucositis, a side effect of tumor chemotherapy. Because of the general cell growth inhibiting effect of TGF-β, they can be used to suppress cancer cells such as for example breast cancer cells.

The involvement of the pituitary hormones, activins and inhibins in modulating the female menstrual cycle is known. Activin induces and inhibin inhibits synthesis of the pituitary hormones FSH and LH. Thus, it is suggested to use polypeptide variants according to the invention to regulate the female menstrual cycle.

Inhibins suppress the development of gonadal tumors. Inhibin-derived polypeptide variants could therefore be applied to prevent and treat gonadal tumors.

Activins are presumed to participate in wound healing. The invention thus encompasses the use of activin-derived polypeptide variants to produce drugs for wound healing.

Activins may be involved in the development and conversion of cartilage to bone. Thus, the activin-derived polypeptide variants may be suited to regulate growth of bone and cartilage.

Activin promotes expansion of blast-forming sub-units and colony-forming sub-units during hematopoiesis, while inhibin inhibits these functions. Therefore, the use of polypeptide variants derived from these proteins is suggested for the regulation of hematopoiesis.

Further particularly important polypeptides that may serve as bases for polypeptide variants are MIS and GDNF (glial cell line derived neurotrophic factor), both of which participate in embryonic development.

In another embodiment, the invention provides a matrix for osteoinduction comprising at least one polypeptide variant and a carrier. Furthermore, an in vitro process is suggested for osteoinduction, using the osteoinductive matrix.

The prior art suggests osteoinductive matrices that contain growth factors. For example, a collagen matrix produced by Integra Life Sciences Corp., which comprises recombinant human BMP-2, is being developed (Hollinger et al., 1998). Also, the company Sofamor-Danek is developing titanium cages containing recombinant human BMP-2. Finally, there is a device named "NOVOS™" manufactured by the company Creative Biomolecules, now being further developed by the company Stryker, that contains osteoinductive type-1 bone collagen and recombinant OP-1 (BMP-7). This device is currently in clinical phase III in the United States of America. Applications include treatment of orthopedic traumas, maxillofacial repairs, and avascular necroses. Also, the use of BMP-7 is suggested for treatment of cartilage damage, kidney failure, brain damage, and bone marrow damage, heart attacks and osteoporosis.

Typically, a matrix material is provided with osteoinductive growth factors, and then the matrix is surgically implanted. The matrix, in this case, is not only a carrier for the growth factor, but also confers physical stability and prevents invasion of soft tissue into the location of bone defects. The addition of growth factors is to speed the replacement of the implant by new bone.

One major problem with the known types of matrices, however, is that the proteins contained in the matrix very rapidly leave the site of application. Because bone repair is a relatively slow process even in the presence of growth factors, the short retention time of the added protein has a limiting effect.

Since the biological effect of osteoinductive growth factors is to induce immigration of pluripotent mesenchymal cells to form chondro precursor cells and osteo precursor cells, and to stimulate their activity, it is necessary to localize the growth factors to the repair site. Growth factors that diffuse away from the repair site, on the one hand, fail in their intended therapeutic purpose, and on the other hand, also pose a threat of causing ectopic bone formation.

The polypeptide variants according to the invention are characterized by an increased heparin-binding ability over known polypeptides, which property can be exploited by using heparin or heparin-like structures as matrix material or as material applied to the matrix to prevent rapid diffusion of polypeptide variants away from the carrier. The polypeptide variants thus remain localized at the site of application. In a preferred embodiment, the carrier should consist of heparin, hydroxyapatite, hyaluronic acid, synthetic polymers, or collagen. The carrier materials may or may not be resorbable.

The prior art discloses various procedures to produce pharmaceutically acceptable matrices. Examples of pharmaceutically acceptable matrices are described in Wagner et al., 1996, and Fischgrund et al., 1997. The matrix may take the form of a block, gel, fleece, sphere, or granules.

Distribution of polypeptide variants within the matrix may or may not be homogenous, but a homogenous distribution would be preferable. The distribution of polypeptide variants may be advantageously configured, depending on the size of the defect or the duration of the healing process. The polypeptide variant concentration within the carrier should range from about 100 μg/$cm^3$ to about 2 mg/$cm^3$, preferably from 250 μg/$cm^3$ to 750 μg/$cm^3$, and particularly preferably from 450 μg/$cm^3$ to 550 μg/$cm^3$. As a rule, a concentration of about 500 μg/$cm^3$ is used.

According to the invention, the osteoinductive matrix may be used to treat orthopedic trauma, maxillofacial repairs, and avascular necroses. Furthermore, it may be recommended for the prevention and treatment of damaged cartilage, kidney failure, brain damage, bone marrow damage, heart attacks, and osteoporosis.

The osteoinductive matrix according to the invention also offers the advantage when using recombinantly produced polypeptide variants that it is free of contamination, e.g. viruses that are observed from time to time with growth factors of animal origin.

The osteoinductive matrix according to the invention may be used in vitro to enable colonization in tissue culture of osteoblasts and/or chondroblasts. The osteoinductive matrices prepared in this way can then be implanted in patients autologously or heterologously by surgical methods (Kübler et al., 1997; Kübler et al., 1998; Chen et al., 1998).

The following figures and examples are intended to explain the invention, but by no means to limit it. The description and examples disclose further embodiments for the person skilled in the art, which should be viewed as included in the invention.

Methods

Measurement of Heparin Binding

Figure 1:
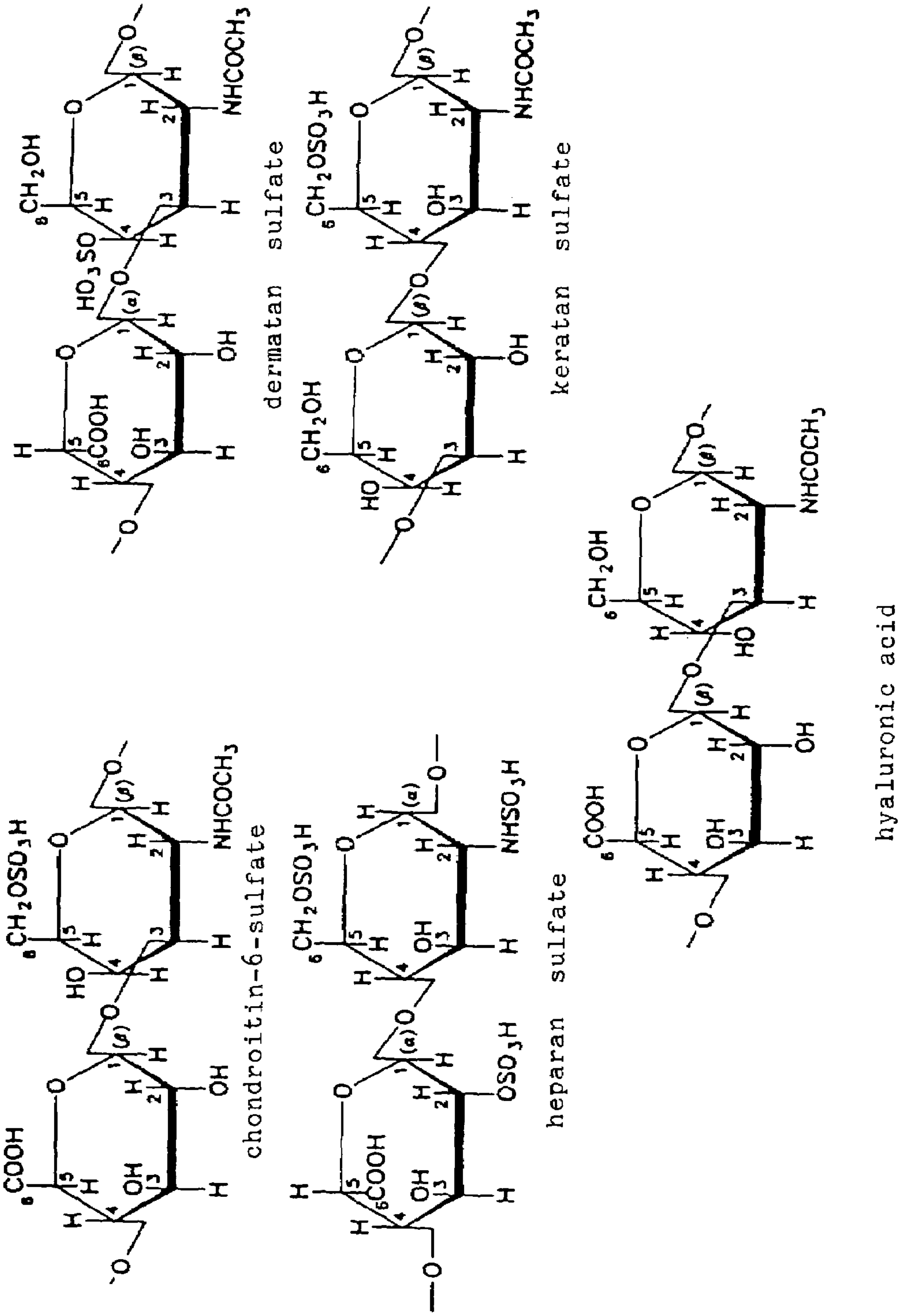
FIG. 1 shows illustrations of a few structural formulae of typical disaccharide units of heparin-like structures as they occur among others in certain glycosaminoglycans.
Figure 2:
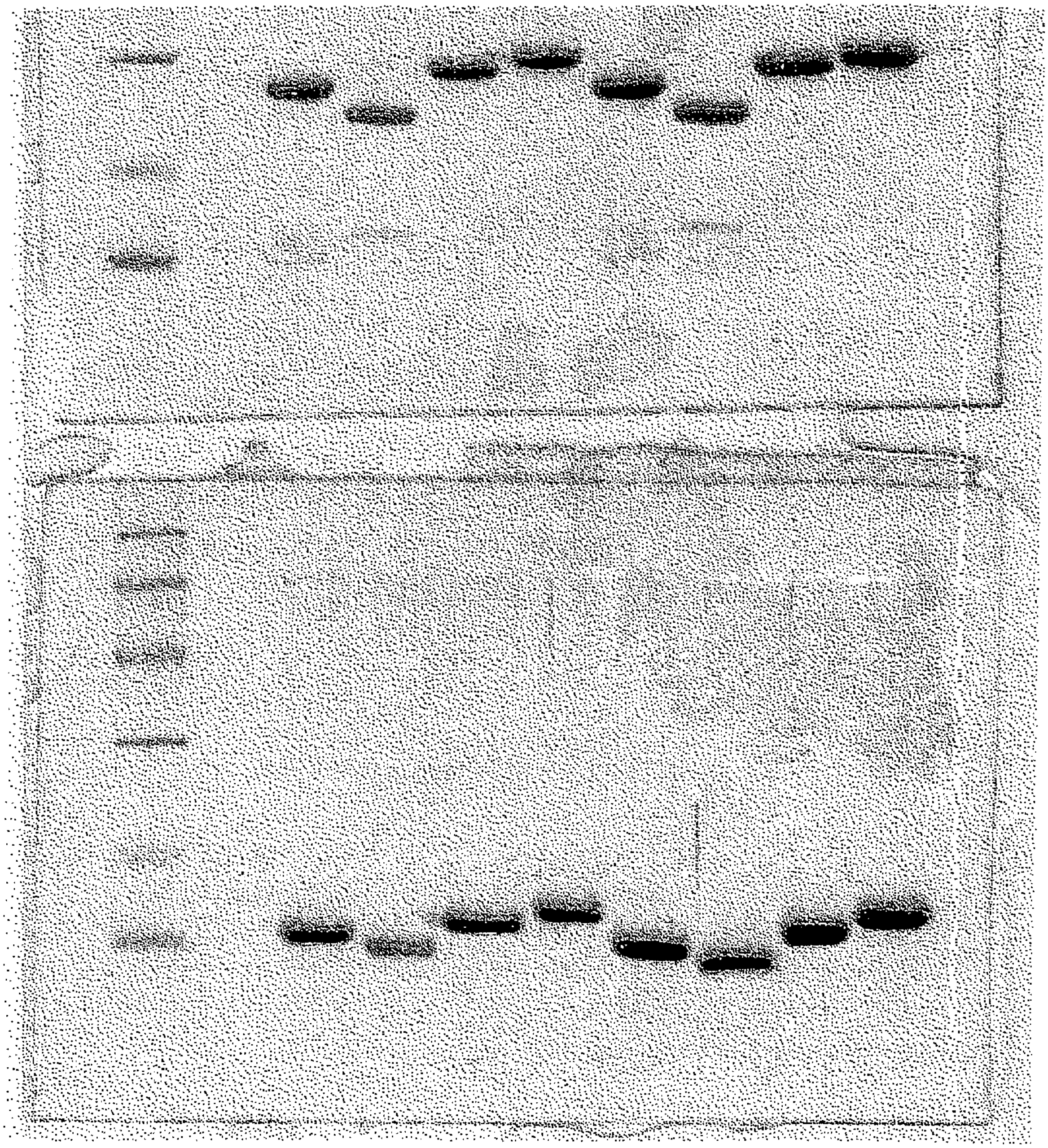
FIG. 2 shows the picture of a Coomassie Blue-stained SDS polyacrylamide gel after separation of variants T3 and T4 as expressed in *E. coli* and then purified, as well as of BMP-2 and EHBMP-2 in oxidized form (above) and reduced form (below). On the left are the molecular weight standards (15, 20, 30, 35, 68, and 94 kD). The gels were loaded as follows (from left to right): lanes 1-4: each 2 μg BMP-2, EHBMP-2, T3 (SEQ ID No.5), and T4 (SEQ ID NO.6); lanes 5-8: each 5 μg BMP-2, EHBMP-2, T3, T4.
Figure 3:
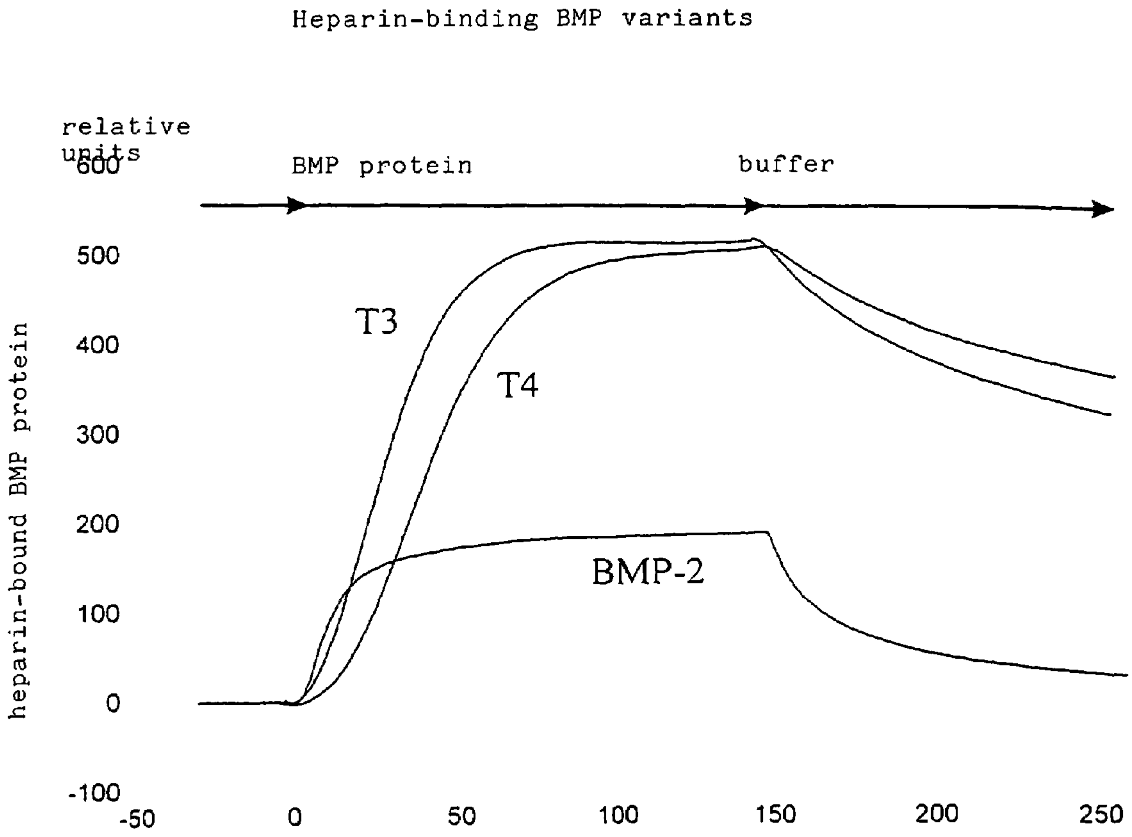
FIG. 3 shows a graphic representation of sensograms recorded with a Pharmacia BIA2000 system of heparin-binding of variants T3 and T4 (SEQ ID Nos. 5 and 6) as well as of BMP-2.
Figure 4:
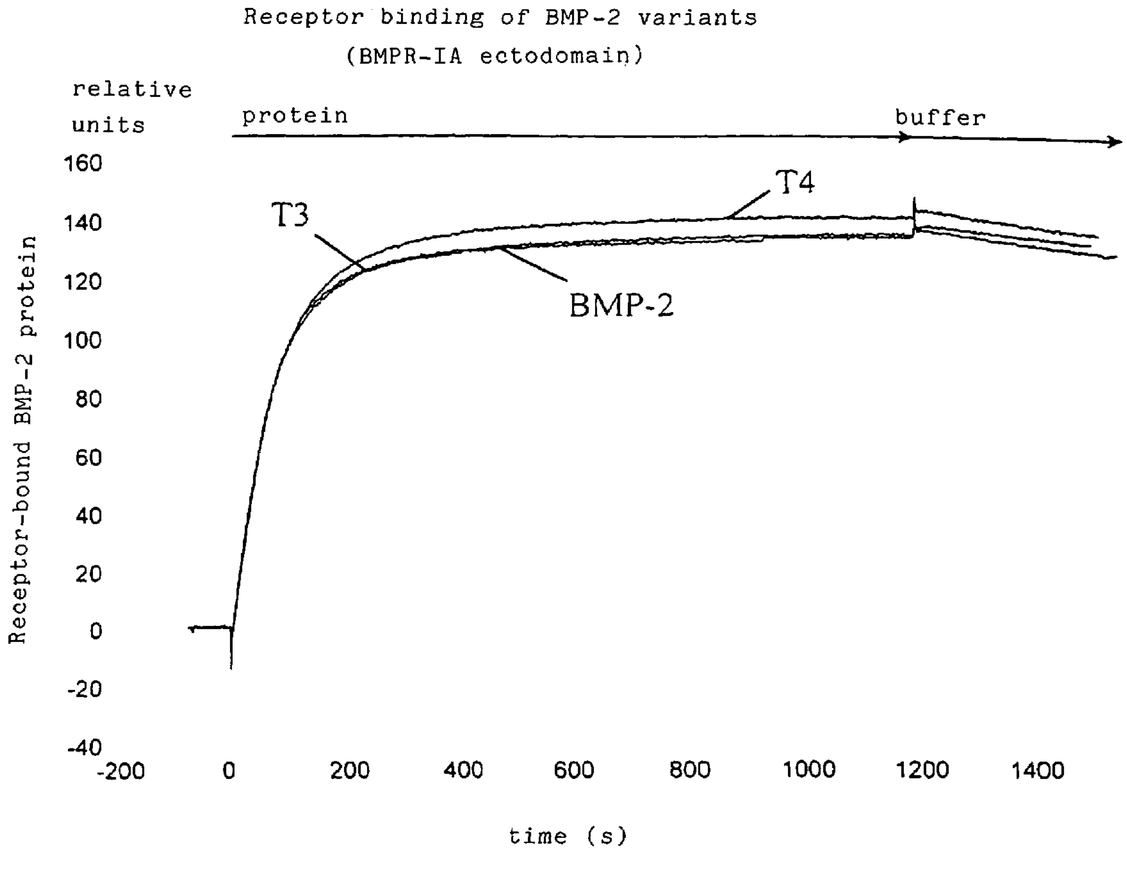
FIG. 4 shows a graphic representation of sensograms recorded with a BIA2000 system of the binding of variants T3 and T4 (SEQ ID Nos. 5 and 6) as well as of BMP-2 to the ectodomain of receptor BMPR-IA.
Figure 5:
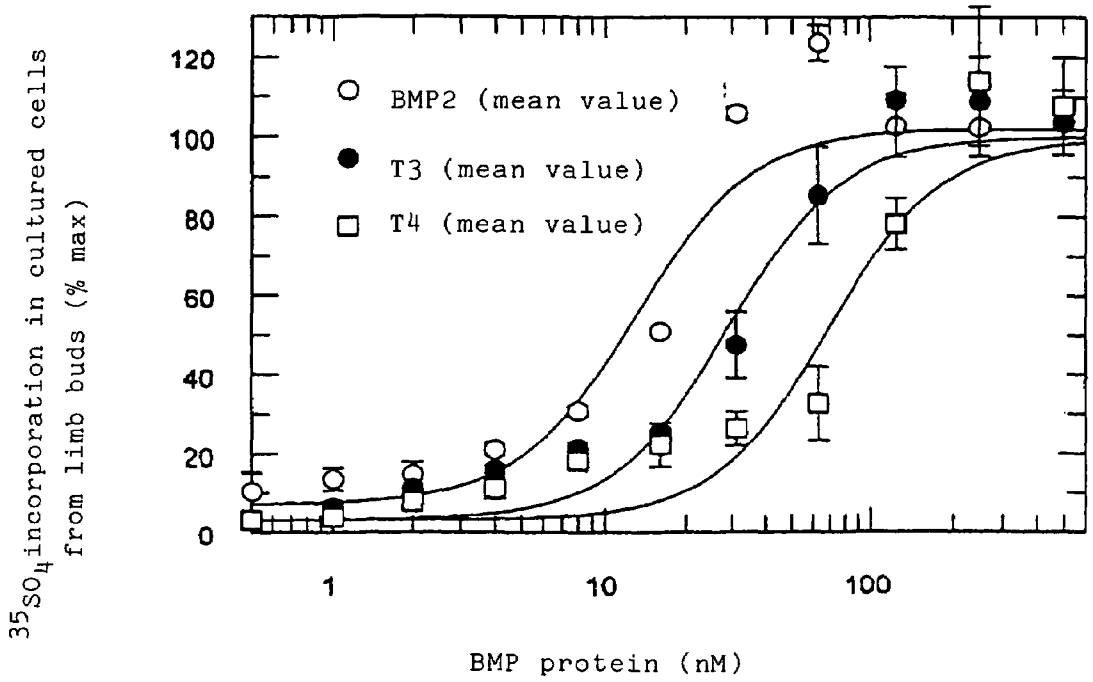
FIG. 5 shows in a graphic representation the incorporation of $^{35}SO_4$ in cells cultured from limb buds of chicken embryos in dependence upon the concentration of BMP-2, variant T3, and variant T4 (SEQ ID Nos. 5 and 6).
Figure 6:
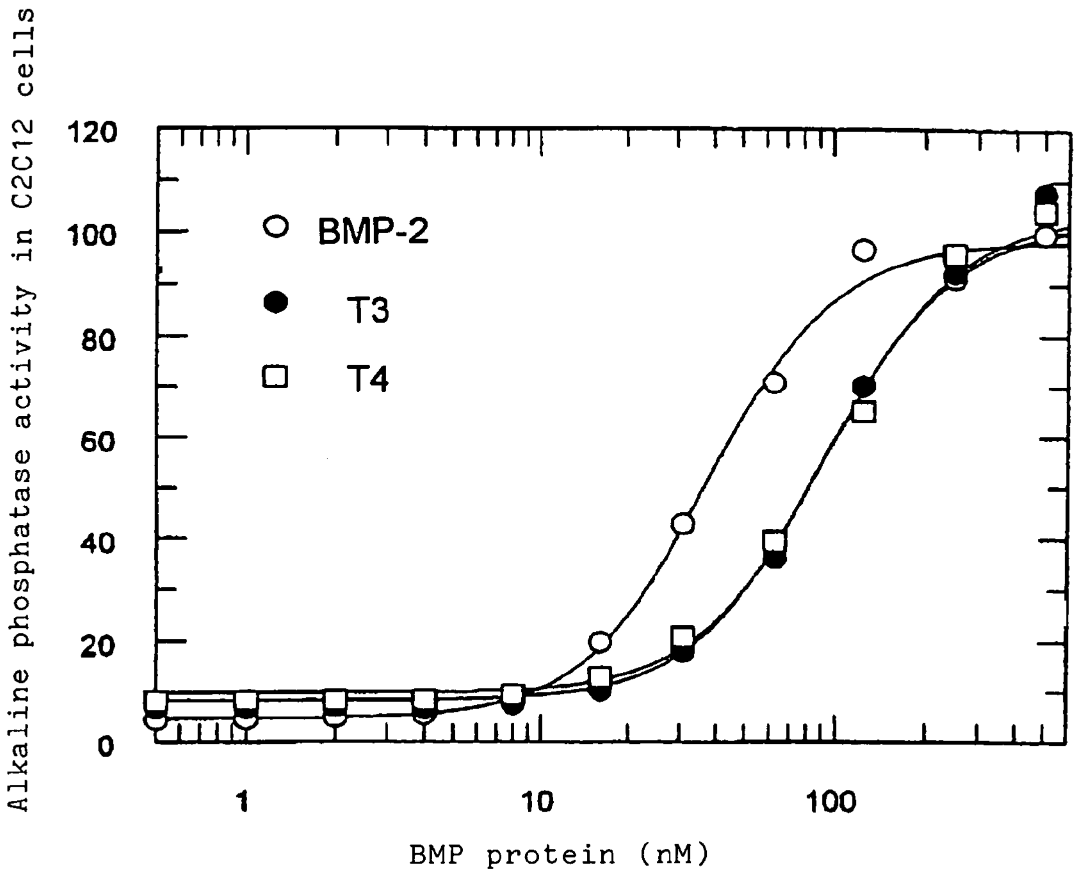
FIG. 6 shows in graphic representation the induction of alkaline phosphatase in cultured C2C12 cells in dependence upon the concentration of BMP-2, variant T3, and variant T4 (SEQ ID Nos. 5 and 6).

To measure heparin-binding, Heparin 6000 was aminobiotinylated (Mach et al., 1993) and fixed to a streptavidin-coated biosensor CM5 (Pharmacia Biosensor AB). The binding of polypeptides and polypeptide variants according to the invention with increased heparin-binding ability to the heparin-doped biosensor was measured with the aid of a BIA2000 instrument. The individual experimental conditions have been described (Ruppert et al., 1996).

Measurement of Binding to Receptor BMPR-IA

To measure the binding, the ectodomain of the receptor BMPR-IA was aminobiotinylated (Shen et al., 1996) and fixed to a streptavidin-coated biosensor CM5 (Pharmacia Biosensor AB). The binding of polypeptides and the polypeptide variants according to the invention to the receptor-doped biosensor was measured with the aid of a BIA2000 instrument.

Measurement of Biological Osteoinduction Activity

The following cell culture system was used to measure the biological activity: Cells were isolated from limb buds of chicken embryos, and used for the measurement of the BMP-dependent incorporation of $^{35}SO_4$ in proteoglycans (Ruppert et al., 1996). A concentration range was chosen for the BMP protein that enabled a determination of both the maximum cell response and the $EC_{50}$ concentration (concentration at which 50% of the maximum incorporation was achieved).

The myoblastic mouse cell line C2C12 was used to determine the BMP-dependent induction of alkaline phosphatase (Katagiri et al., 1994). It was possible to determine both the maximum cell response and $EC_{50}$ concentration.

EXAMPLE 1

Expression and Characterization of T3 cDNA (Ruppert et al., 1996) encoding mature human BMP-2 (NIH database Entrez/Swiss-Prot No. P12643) and, in addition, ATGGCT (Met-Ala) at the 5' end was subjected to cassette mutagenesis (Wang et al., 1997). Between the singular cleavage sites for NcoI and AflII, the following double-stranded DNA was inserted:

5'CATGGCTCAAGCCAAACACAAACAGCG-GAAACGCGCTCGTAAACGTC 3'SEQ ID No. 9

3'CGAGTTCGGTTTGTGTTTGTCGC-CTTTGCGCGAGCATTTGCAGAATT 5'SEQ ID No. 10

Thus, the sequence Arg-Lys-Arg-Ala (SEQ ID No. 3) was additionally inserted between Gln at position 8 and Arg at position 9 of a human Met-Ala-BMP-2. The mutated cDNA was integrated as a NcoI/BamHI fragment into expression vector pRBSIIP$_{N25}$x/o (Stueber et al., 1984), and the mutation was verified by sequencing.

After expression and isolation, it was shown by SDS polyacrylamide gel electrophoresis (SDS-PAGE) that the variant T3 produced in this method had a greater apparent molecular weight in comparison to BMP-2, as expected. T3 interacted in biosensor experiments (BIA2000) with unaltered affinity (dissociation constant $K_d$: approx. 200 pM) with the ectodomain of the BMP receptor BMPR-IA (NIH database Entrez/Swiss-Prot No. P36894). The binding to heparin, however, was increased relative to that of BMP-2, whereas dissociation had decelerated.

The biological activity was altered in different test systems. The proteoglycan synthesis measured via sulfate incorporation in cells of limb buds of chicken embryos showed a higher $EC_{50}$ value for T3 in comparison to BMP-2. The maximum achievable incorporation remained unchanged. The induction of alkaline phosphatase activity in the C2C12 cell line also showed a higher $EC_{50}$ value for T3 than for BMP-2.

EXAMPLE 2

Expression and Characterization of T4

Example 1 was repeated with the difference that the following double-stranded DNA was integrated into BMP-2 cDNA:

5'CATGGCTCAAGCCAAACACAAACAGCG-GAAACGCGCTAAGCATAAGCAACGTAAGCGTC3'

3'CGAGTTCGGTTTGTGTTTGTCGC-CTTTGCGCGATTCGTATTCGTTGCAT-TCGCAGAATT5'

The upper sequence was given as SEQ ID No. 11, the lower one as SEQ ID No: 12 in the sequence listing.

Thus, the sequence Arg-Lys-Arg-Ala-Lys-His-Lys-Gln was additionally inserted between Gln at position 8 and Arg at position 9 of BMP-2.

Expressed and isolated, variant T4 was shown by SDS-PAGE to have a higher apparent molecular weight than T3 and BMP-2. T4 binds to the ectodomain of BMP receptor BMPR-IA with a dissociation constant of about 340 pM. This correlates to the receptor affinity of BMP-2 ($K_d$ 320 pM). The binding of T4 to heparin, however, was higher in comparison to BMP-2, and the dissociation (away) decelerated. The release of T4 from heparin was surprisingly slower than that of T3.

The biological activity of T4 is altered relative to BMP-2. T4 shows a higher $EC_{50}$ value than BMP-2 (and even higher than T3) during proteoglycan synthesis (sulfate incorporation) in limb bud cells of chicken embryos. Likewise, T4 induces activity of alkaline phosphatase in C2C12 cells at a higher $EC_{50}$ value than does BMP-2.

EXAMPLE 3

Studies on In Vivo Efficiency of Polypeptide Variants

The method chosen here was the induction of ectopic bones in the thigh muscle of the mouse. Ectopic bone formation means that bone is formed de novo in foreign tissue and without contact to the skeletal system. The advantage of this test system comes from its high stringency. Because there is no contact to any skeletal bone, regenerative bone healing processes do not play any roll. Thus, false positive test results are ruled out such as those that may result from bone damage occurring during surgery.

The method to induce ectopic bone formation in ICR mice is described in detail in Kübler and Urist, 1991.

BMP-2 and variant T3 were mixed with bovine serum albumin as carrier in various concentrations, and implanted into the quadriceps femoris muscles of ICR mice. After three weeks, the newly formed bone material was characterized by X-ray imaging and histological examinations.

Figure 7:
FIGS. 7*a* and 7*b* show histological views of ossicles formed in mouse, which were induced by implantation of BMP-2. The preparations were stained with hematoxylin eosin. Ossicles appear violet enclosing white or dark violet areas. The dark violet areas indicate bone marrow, the white cells are fatty tissue that naturally occurs in bone marrow. The surrounding muscle tissue is stained deep red.
Figure 7:
Figure 8:
FIG. 8 shows the histological view of an ossicle formed in mouse, which was induced by treating it with T3. The preparation was also stained with hematoxylin eosin.

The implantation of bovine serum albumin without BMP (control) resulted in no detectable bone formation. No symptoms of inflammation or other injurious side effects were observed in the case of BMP or T3. FIG. 7 indicates that BMP-2 could induce the formation of bone matrix and bone marrow. FIG. 8 shows the correlative treatment with T3. In comparison to the result with BMP-2, it becomes apparent for T3 that the ratio of bone matrix to bone marrow is strongly shifted to a high amount of bone matrix.

Figure 9:
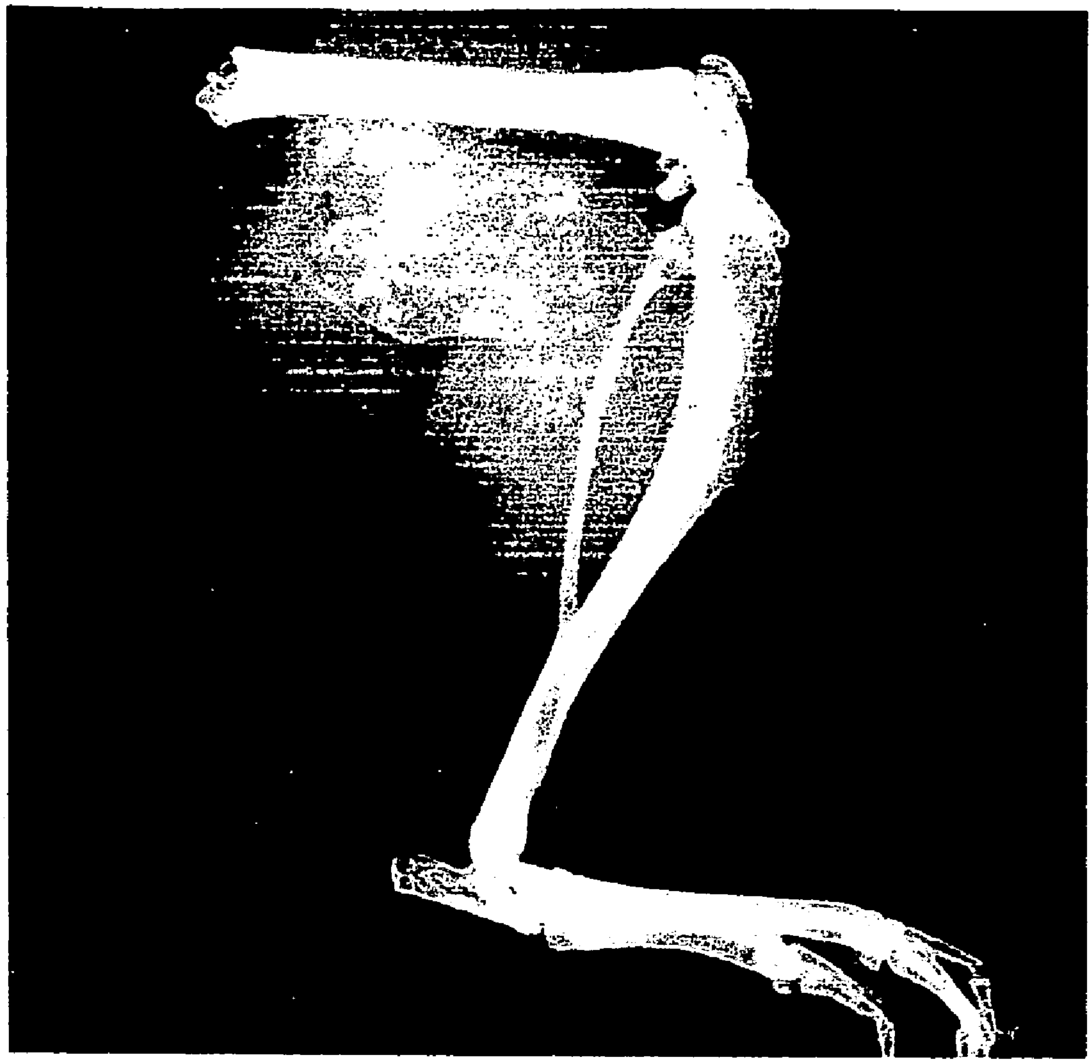
FIG. 9 shows an X-ray picture of an ossicle formed in mouse by a T3 implant.

FIG. 9 shows an X-ray image of an ossicle formed by T3 implantation. The size of the ossicle does not significantly differ from that of ossicles resulting from conventional BMP treatment in the same test system.

Figure 10:
FIG. 10 shows the histological view of an ossicle formed in mouse, which was induced by treatment with T3.

FIG. 10 shows the histological view of an ossicle that was induced by treatment with T3.

The staining was performed with Masson-Trichrome which allows one to distinguish the stages of differentiation of bone tissue. The color red indicates completely differentiated bones, turquoise stained areas in the process of ossification. In some parts, one can make out round white cells within the turquoise stained tissue; these are residual parts of cartilage-forming chondrocytes, because BMP-induced bone formation involves endochondral ossification (transient cartilage formation).

The experiments underlying FIGS. 7 through 10 are performed using each 10 μm of recombinant human BMP-2 or recombinant T3 (SEQ ID No. 5). The following table compares the in vivo efficiency of BMP-2 and recombinant T3.

TABLE 1

Comparison of bone formation induced by BMP-2 and T3.

| rhBMP-2 (μg) | T3 (μg) | Bone Formation |
|---|---|---|
| — | — | 0/30 |
| 0.4 | — | 0/3 |
| — | 0.4 | 3/4 |
| 1 | — | 0/9 |
| — | 1 | 4/4 |
| 4 | — | 3/3 |
| — | 4 | 4/4 |
| 10 | — | 10/11 |
| — | 10 | 4/4 |

The comparison shows that at low concentrations T3 is more effective than BMP-2 (Table 1). In the case of implantation of 1 μg of BMP-2, bone formation was not observed in any of the nine tests, whereas bones were formed in four out of four implanted animals at the same amount of T3. T3 induced bone formation even in three of four animals using only 0.4 μg.

The results show that the polypeptide variants with increased heparin-binding ability can induce bone formation in vivo. There were no cases of inflammation reaction or other intolerance. In comparison to conventional BMP-2, the treatment with T3 induces formation of an ossicle with considerably higher bone matrix content. Because the matrix gives the bone its mechanical stability, a bone with greater density will have more solidity and greater functional ability to bear weight. Thus it will induce the formation of bone with significantly higher quality in comparison to BMP-2. Because T3 shows biological activity in vivo at lower concentrations than BMP-2, its use will reduce the necessary amount of growth factor. This is a desirable advantage of the polypeptide variant over BMP-2.

BIBLIOGRAPHY

Altschul et al., J. Mol. Biol. 215 (1990), 403410

Altschul et al., BLAST manual, NCB NLM NIH Bethesda Md. 20894

Chen et al., Neurosurg. Focus 4 (1998), article 11

Devereux et al., Nucleic Acid Res. 12 (1984), 387

Fischgrund et al., J. Spinal Disorder 10 (1997), 467472

Henikoff & Henikoff, PNAS USA 89 (1992), 10915-10919

Hollinger et al., J. Biomed. Mater. Res. 43 (1998), 356-364

Katagiri et al., J. Cell. Biol. 127 (1994), 1755-66; erratum published in J. Cell. Biol. 128 (1995), 714

Kingsley, Genes Dev. 8 (1994), 133-146

Kübler et al., Dtsch. Zahnärztl. Z. 53 (1998), 834-843

Kübler et al., Mund-, Kiefer-, Gesichtschirurgie 1 (1997), 2-25

Kübler et al., Mund-, Kiefer-, Gesichtschirurgie 3 (Suppl. 1) (1999), 134-139

Kübler & Urist, J. Craniomaxillofac. Surg. 19 (1991), 283-288

Mach et al., Biochemistry 32, (1993), 5480-89

Maniatis et al., Molecular Cloning (1989), Cold Spring Harbor Laboratory Press

McDonald & Hendrickson, Cell 73 (1993), 421-24

Needleman & Wunsch, J. Mol. Biol. 48 (1970), 443-453 Recombinant Gene Expression Protocols, ed. R. S. Tuan Methods in Molecular Biology 62 (1995), Humana Press, Totowa, N.J.

Reddi, Nature Biotechnol. 16 (1998), 247-52

Ruppert et al., Eur. J. Biochem. 237 (1996), 295-302

Shen et al., Eur. J. Biochem. 240 (1996), 252-261

Stueber et al., EMBO J. 3 (1984), 3143-3148

Wagner et al., J. Surg. Res. 66 (1996), 100-108

Wang et al., PNAS 94 (1997), 1657-62

Weigel et al., Eur. J. Biochem. 180 (1989), 295-300

---

The invention claimed is:

1. A bone morphogenetic protein (BMP) or a growth differentiation factor (GDF) polypeptide variant with increased heparin-binding ability, characterized in that (i) added to the amino acid sequence of a BMP or GDF polypeptide is at least one oligopeptide comprising the amino acid sequence $X_1X_2X_3X_4X_5X_6$; and/or (ii) inserted into the amino acid sequence of a BMP or GDF polypeptide is at least one oligopeptide comprising the amino acid sequence $X_1X_2X_3X_4X_5X_6$; and/or (iii) at least one oligopeptide sequence naturally occurring within the amino acid sequence of a BMP or GDF polypeptide is substituted by an oligopeptide comprising an amino acid sequence $X_1X_2X_3X_4X_5X_6$, wherein $X_1$=K, R, or H;

$X_2$=K, R, or H;

$X_3$=K, R, or H;

$X_4$=not K, R, H, but any other amino acid;

$X_5$=not K, R, H, but any other or no amino acid;

$X_6$=not K, R, H, but any other or no amino acid (SEQ ID NO: 1).

2. The BMP or GDF polypeptide variant as recited in claim 1, characterized in that one to four copies of said oligopeptide are inserted at one to four positions within the BMP or GDF polypeptide.

3. The BMP or GDF polypeptide variant as recited in claim 1, characterized in that said oligopeptide is added to the N-terminus and/or inserted into the N-terminal region, and/or substitutes a part of the N-terminal region.

4. The BMP or GDF polypeptide variant as recited in claim 1, characterized in that the amino acid sequence of said BMP or GDF polypeptide variant further contains a sequence of relevance to recombinant expression at the N-terminus, said sequence of relevance to recombinant expression being M or MZ, where M stands for methionine and Z stands for one or more amino acids.

5. The BMP or GDF polypeptide variant as recited in claim 1, characterized in that said BMP or GDF polypeptide variant further contains a His-tag.

6. The BMP or GDF polypeptide variant as recited in claim 1, characterized in that said BMP or GDF polypeptide is altered by addition, substitution, insertion, inversion, and/or deletion, where said BMP or GDF polypeptide altered by addition, substitution, insertion, inversion and/or deletion shows at least 50% receptor binding affinity to the ectodomain of BMPR-IA as BMP-2, and at least 90% homology to the unaltered BMP or GDF polypeptide.

7. The BMP or GDF polypeptide variant as recited in claim 1, characterized in that said BMP or GDF polypeptide is BMP-2, BMP4, BMP-5, BMP-6, BMP-7/OP-1, BMP-8/OP-2, or GDF5.

8. The BMP or GDF polypeptide variant as recited in claim 1, wherein the BMP or GDF polypeptide has a cysteine knot, characterized in that said oligopeptide is inserted before the cysteine knot.

9. The BMP or GDF polypeptide variant as recited in claim 1, characterized in that said BMP or GDF polypeptide variant is a polymer, oligomer, or dimer.

10. A nucleic acid molecule, comprising a nucleic acid sequence encoding a BMP or GDF polypeptide variant as recited in claim 1.

11. The nucleic acid molecule as recited in claim 10, characterized in that said nucleic acid sequence is derived from genomic DNA or cDNA, or is a synthetic DNA.

12. The nucleic acid molecule as recited in claim 10, further comprising a promoter suited to control expression, wherein said nucleic acid sequence encoding a BMP or GDF polypeptide variant is under the control of said promoter.

13. A vector comprising the nucleic acid molecule as recited in claim 10, wherein said nucleic acid molecule further comprises at least part of a vector.

14. An isolated host cell, containing a nucleic acid molecule as recited in claim 10, wherein said host cell is a prokaryotic or eukaryotic cell suitable for expression of said nucleic acid molecule.

15. A process for producing a BMP or GDF polypeptide variant with increased heparin-binding ability as recited in claim 1, comprising:

addition to the amino acid sequence of a BMP or GDF polypeptide of at least one oligopeptide containing an amino acid sequence selected from SEQ ID NO:1; and/or insertion into the amino acid sequence of a BMP or GDF polypeptide of at least one oligopeptide containing an amino acid sequence selected from SEQ ID NO:1; and/or substitution of at least one oligopeptide sequence naturally occurring within the amino acid sequence of a BMP or GDF polypeptide by one oligopeptide containing an amino acid sequence selected from SEQ ID NO:1.

16. The process as recited in claim 15, characterized in that said process comprises a chemical and/or enzymatic synthesis process.

17. The process as recited in claim 15, characterized in that said process comprises gene technological processes.

18. The process as recited in claim 15, characterized in that said process comprises:

a) in vitro mutagenesis of a nucleic acid encoding a BMP or GDF polypeptide, so that (i) to the nucleic acid encoding said BMP or GDF polypeptide is added at least one nucleic acid encoding an oligopeptide containing an amino acid sequence that is selected from SEQ ID NO:1; and/or (ii) into the nucleic acid encoding said BMP or GDF polypeptide is inserted at least one nucleic acid encoding an oligopeptide containing an amino acid sequence that is selected from SEQ ID NO:1; and/or (iii) at least one nucleic acid sequence naturally occurring within the nucleic acid sequence encoding said BMP or GDF polypeptide is substituted by a nucleic acid sequence encoding an oligopeptide containing an amino acid sequence selected from SEQ ID NO:1;

b) cloning of the mutated nucleic acid into a suitable expression vector;

c) transformation/transfection of a suitable host cell with the expression vector obtained;

d) cultivation of said transformed/transfected host cell under conditions suitable for expression;

e) isolation, and if necessary renaturation, of the expressed polypeptide variant.

19. The process as recited in claim 15, characterized in that said process is carried out within a prokaryotic host cell.

20. The process as recited in claim 19, wherein the prokaryotic host cell is *E. coli*.

21. The process as recited in claim 15, characterized in that said process is carried out within a eukaryotic cell.

22. The process as recited in claim 21, wherein the eukaryotic cell is selected from the group consisting of a yeast cell, a plant cell, an insect cell, CHO cells, and COS cells.

23. A pharmaceutical composition for stimulating osteogenesis, chondrogenesis, and/or wound healing, comprising a BMP or GDF polypeptide variant as recited in claim 1 and a physiologically compatible additive.

24. A composition, comprising a BMP or GDF polypeptide variant as recited in claim 1 and a carrier selected from among heparin, hydroxyapatite, hyaluronic acid, synthetic polymers, and collagen.

25. A matrix, characterized in that said matrix contains or is coated with heparin or heparin-like substances and BMP or GDF polypeptide variants as recited in claim 1 are adsorbed to said heparin or heparin-like substances.

26. The BMP or GDF polypeptide variant as recited in claim 1, characterized in that said BMP or GDF polypeptide is altered by addition, substitution, insertion, inversion, and/or deletion, where said BMW or GDF polypeptide altered by addition, substitution, insertion, inversion and/or deletion shows at least 90% receptor binding affinity to the ectodomain of BMPR-IA as BMP-2, and at least 90% homology to the unaltered BMP or GDF polypeptide.

27. A bone morphogenetic protein (BMP) or a growth differentiation factor (GDF) polypeptide variant with increased heparin-binding ability, characterized in that (i) added to the amino acid sequence of a polypeptide is at least one oligopeptide comprising the amino acid sequence RKRA (SEQ ID NO:3) or RKRAKHKQ (SEQ ID NO:4); and/or (ii) inserted into the amino acid sequence of a polypeptide is at least one oligopeptide comprising the amino acid sequence RKRA (SEQ ID NO:3) or RKRAKHKQ (SEQ ID NO:4); and/or (iii) at least one oligopeptide sequence naturally occurring within the amino acid sequence of a polypeptide is substituted by an oligopeptide comprising an amino acid sequence RKRA (SEQ ID NO:3) or RKRAKHKQ (SEQ ID NO:4).

28. A bone morphogenetic protein 2 BMP-2) polypeptide variant with increased heparin-binding ability, characterized in that said BMP-2 polypeptide variant has the amino acid sequence SEQ ID NO:5 (T3) or SEQ ID NO:6 (T4).

* * * * *